United States Patent
Shinohara et al.

(10) Patent No.: US 7,769,223 B2
(45) Date of Patent: Aug. 3, 2010

(54) SURFACE DEFECT INSPECTOR AND METHOD OF INSPECTING SURFACE DEFECT

(75) Inventors: Hiroaki Shinohara, Minami-ashigara (JP); Minoru Matsuura, Minami-ashigara (JP)

(73) Assignee: FUJIFILM Corporation, Tokyo (JP)

( * ) Notice: Subject to any disclaimer, the term of this patent is extended or adjusted under 35 U.S.C. 154(b) by 867 days.

(21) Appl. No.: 11/655,212

(22) Filed: Jan. 19, 2007

(65) Prior Publication Data
US 2007/0165941 A1    Jul. 19, 2007

(30) Foreign Application Priority Data
Jan. 19, 2006    (JP)    ............... 2006-010860

(51) Int. Cl.
*G06K 9/00*    (2006.01)
(52) U.S. Cl. ............... 382/141; 348/86; 348/125; 356/237.1
(58) Field of Classification Search ......... 382/141–152; 250/306–311; 348/86–95, 125–134; 700/95–212; 29/833; 438/16; 356/237.1–237.6, 426–431; 702/35–40
See application file for complete search history.

(56) References Cited

U.S. PATENT DOCUMENTS

| | | | |
|---|---|---|---|
| 3,794,427 A * | 2/1974 | Shibata et al. | 356/613 |
| 4,603,956 A * | 8/1986 | Baker | 396/569 |
| 4,730,213 A * | 3/1988 | Kelly et al. | 348/135 |
| 4,853,777 A * | 8/1989 | Hupp | 348/128 |
| 5,270,794 A * | 12/1993 | Tsuji et al. | 356/600 |
| 5,499,094 A * | 3/1996 | Swierczek | 356/121 |
| 6,023,333 A * | 2/2000 | Laux et al. | 356/600 |
| 6,909,502 B2 * | 6/2005 | Capaldo et al. | 356/239.2 |
| 6,930,772 B2 * | 8/2005 | Maezono et al. | 356/239.1 |
| 6,980,291 B2 * | 12/2005 | Saito | 356/237.2 |
| 7,164,145 B2 * | 1/2007 | Shakespeare | 250/559.09 |
| 7,345,698 B2 * | 3/2008 | Abbott et al. | 348/86 |
| 2004/0057046 A1 * | 3/2004 | Abbott et al. | 356/239.1 |
| 2004/0179193 A1 * | 9/2004 | Maezono et al. | 356/239.1 |
| 2005/0105791 A1 * | 5/2005 | Lee et al. | 382/145 |
| 2007/0165941 A1 * | 7/2007 | Shinohara et al. | 382/149 |
| 2009/0257141 A1 * | 10/2009 | Yamada et al. | 359/893 |

FOREIGN PATENT DOCUMENTS

JP    3-135704 A    6/1991

* cited by examiner

*Primary Examiner*—Aaron W Carter
(74) *Attorney, Agent, or Firm*—Sughrue Mion, PLLC

(57) ABSTRACT

Wrinkles on polymer film as surface defect are inspected. The film is transported on an inspecting surface having a color for absorbing light. A dot pattern having dots on a transparent test chart sheet, facing the film, is photographed by image pickup upon reflection of the dot pattern on the film positioned on the inspecting surface. A length of the dots being photographed is measured according to image data, to obtain length information of 1-5. A length data table of the dots is created by arranging the length information of 1-5 at locations of the dots. Occurrence of a wrinkle is determined at one of the locations if a difference between the dots occurs in the length information of 1-5 in the length data table. To a rear of the test chart sheet, inspecting light is applied, passes through, and becomes incident upon the film.

28 Claims, 11 Drawing Sheets

FIG. 8A
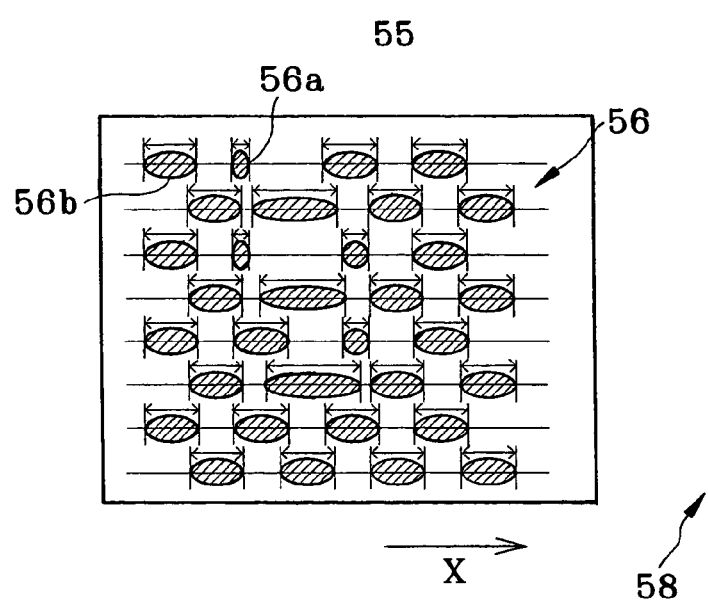
FIG. 8B
| 3 | 1 | 3 | 3 |
| 3 | 5 | 3 | 3 |
| 3 | 1 | 2 | 3 |
| 3 | 5 | 3 | 3 |
| 3 | 3 | 2 | 3 |
| 3 | 5 | 3 | 3 |
| 3 | 3 | 3 | 3 |
| 3 | 3 | 3 | 3 |
FIG. 8C
FIG. 8D
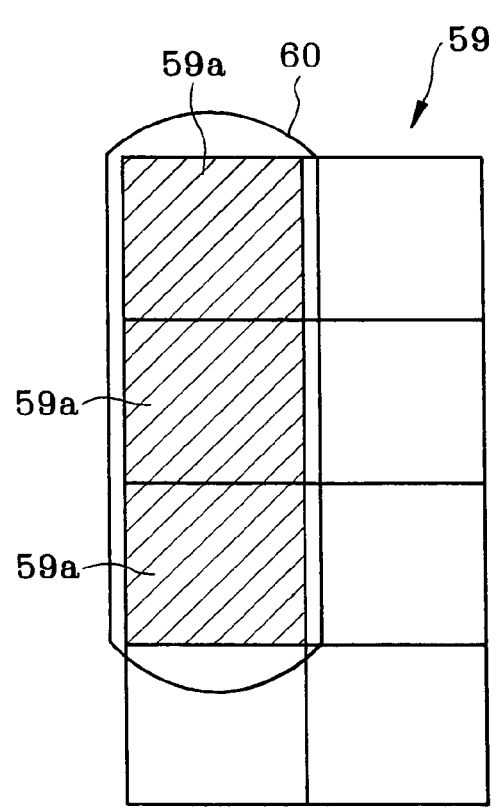

FIG. 12A (PRIOR ART)
FIG. 12B (PRIOR ART)
FIG. 12C (PRIOR ART)
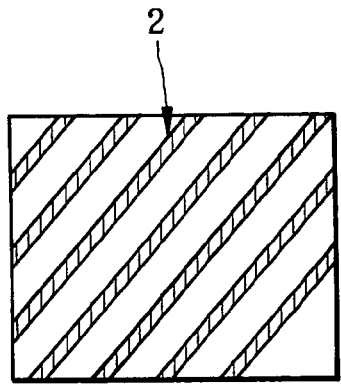
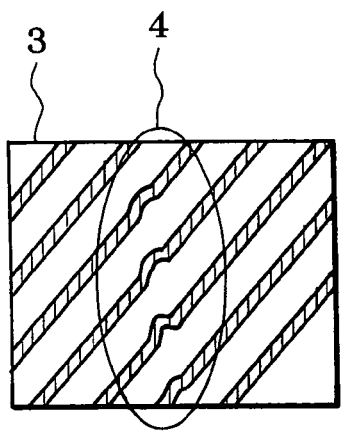
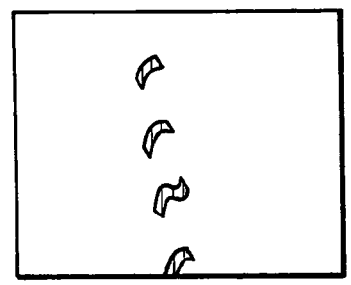
FIG. 13A (PRIOR ART)
FIG. 13B (PRIOR ART)
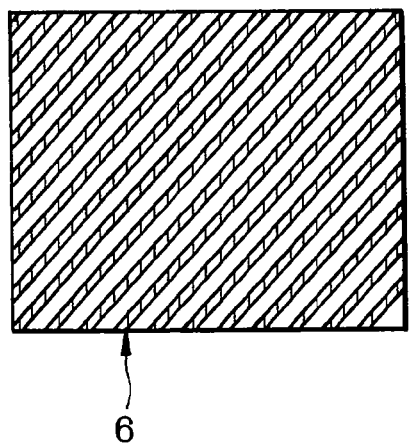
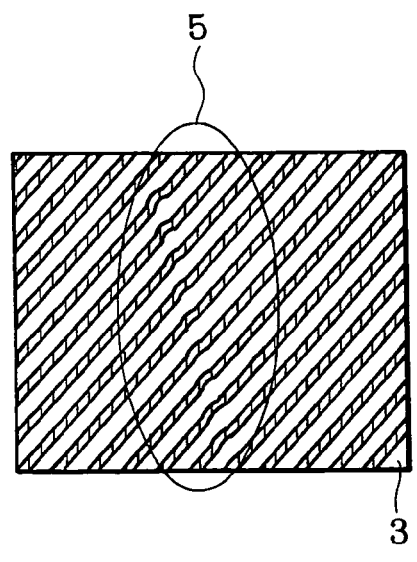

SURFACE DEFECT INSPECTOR AND METHOD OF INSPECTING SURFACE DEFECT

BACKGROUND OF THE INVENTION

1. Field of the Invention

The present invention relates to a surface defect inspector and a method of inspecting a surface defect. More particularly, the present invention relates to a surface defect inspector and a method of inspecting a surface defect, in which a surface defect with a small depth, such as a wrinkle, can be inspected and detected reliably.

2. Description Related to the Prior Art

Cellulose acylate film is polymer film having high performance owing to optically isotropic property, and widely used as protection film of a polarization plate of a liquid crystal display device, an optical compensatory film, and the like. Among various examples, cellulose triacetate film is specifically used.

Cellulose acylate film is produced by solution casting. Polymer or cellulose acylate is dissolved in organic solvent, to prepare polymer solution, which is generally referred to as dope. In a caster, the dope is cast on a support, to form cast film. When the cast film comes to have a self-supporting property with time, polymer film is formed and stripped from the support. A tentering machine is supplied with the polymer film, which is transported while its selvedge portions are clipped for stretching. The polymer film is dried and also oriented in the width direction. An edge slitter is disposed downstream from the tentering machine, and slits away the selvedge portions. Then the polymer film is passed through a drier, and then wound by a winder.

The production of the cellulose acylate film is strictly managed by use of various techniques. However, it is extremely difficult to produce completely defect-free products of the polymer film due to incidental presence of foreign particles and occurrence of wrinkles and unevenness in the thickness of the polymer film. In particular, the occurrence of the wrinkle causes a serious problem for the quality of cellulose acylate film and any types of the polymer film.

There is a known inspection of the wrinkle on the polymer film. A roller of a black color is used. A polymer film 3 is supported on the roller. In FIG. 12A, a pattern of stripes 2 is projected on the polymer film 3 by use of an illuminating light source. When the wrinkle exists on the polymer film 3, a distortion occurs on lines of the stripes 2 in an indicated portion 4 of FIG. 12B. This state is photographed by a camera, to retrieve distinct portions between the obtained image and an image in FIG. 12A. The retrieved image of FIG. 12C is subjected to image processing, to detect finely protruded or recessed pattern of the wrinkle on the surface of the polymer film 3.

A method of inspecting distortion of plates in place of the polymer film is known. JP-A 3-135704 discloses such a method of inspecting reflection distortion or transmission distortion of a glass plate or the like. A test pattern containing bright and dark portions of spots or lines is picked up by use of the glass plate. The distortion is detected by image processing of image data of an image obtained by the image pickup.

Also, inclined wrinkles are likely to occur in the vicinity of the selvedge portions in a section between the tentering machine and edge slitter. The inclined wrinkles are inclined relative of the running of the polymer film 3. As the inclined wrinkles have a small depth, has a small length, and occurs continually. It is impossible to detect the inclined wrinkles even by human eyes, micro meters, laser inspector or the like. In FIG. 13A, stripes 6 are included in a test pattern, and have a smaller interval than that between the stripes 2 of FIG. 12A for detecting the wrinkle. In FIG. 13B, an indicated portion 5 has distortion of lines of the stripes 6. The distortion is so small that inspection of the inclined wrinkles is highly difficult. In addition to the inclined wrinkles, fine wrinkles or other small defects are difficult to find in the above inspecting method.

SUMMARY OF THE INVENTION

In view of the foregoing problems, an object of the present invention is to provide a surface defect inspector and a method of inspecting a surface defect, in which a surface defect with a small depth, such as a wrinkle, can be inspected and detected reliably.

In order to achieve the above and other objects and advantages of this invention, a surface defect inspecting method includes transporting film on an inspecting surface having a color for absorbing light. A dot pattern having dots on a dot pattern test chart is photographed by image pickup upon reflection of the dot pattern on the film positioned on the inspecting surface. A length of the dots being photographed is measured according to image data obtained by the image pickup, to obtain length information. A length data table of the dots is created by arranging the length information at locations of the dots. Occurrence of a surface defect is determined at one of the locations if a difference between the dots occurs in the length information in the length data table.

The dots have a diameter equal to or more than 1 mm and equal to or less than 3 mm, and are arranged at a pitch equal to or more than 3 mm and equal to or less than 5 mm.

The dots are arranged so that dots in a first dot array thereof are offset in a zigzag manner from dots in a second dot array thereof.

The dots have a black color.

A transparent test chart sheet constitutes the test chart and is disposed to face the film. Inspecting light is applied to a rear of the test chart sheet, passes through, and becomes incident upon the film.

The inspecting surface is a peripheral surface of an inspecting roller, and a diameter of the inspecting roller is equal to or more than 250 mm and equal to or less than 500 mm.

The peripheral surface of the inspecting roller is finished by mat finish.

The film contacts on the inspecting roller at a wrap angle equal to or more than 120 degrees and equal to or less than 180 degrees.

The determining step includes classifying the dots into an acceptable dot and an unacceptable dot in the length data table according to the length. The length data table is split into blocks with a prescribed area, to acquire amounts of the unacceptable dot per the blocks. If the amounts of the unacceptable dot per the blocks are more than a prescribed value, suspected defective blocks therewith retrieved among the blocks are determined. A suspected defective pattern is defined by continuation of adjacent suspected defective blocks among the suspected defective blocks. The surface defect is determined from the suspected defective pattern by evaluating a shape thereof.

The acceptable dot has a length of length information equal to a predetermined middle rank length information, and the unacceptable dot has a length of length information higher or lower than the predetermined middle rank length information.

The surface defect is constituted by a wrinkle on the film.

Adjacent suspected defective blocks being consecutive in any one of vertical, horizontal and diagonal directions are retrieved among the suspected defective blocks, and combined to define a defective pattern, and the wrinkle is constituted by the defective pattern.

The wrinkle is graded in prescribed grades according to a number of the suspected defective blocks.

In a preferred embodiment, the suspected defective blocks are plotted at points defined on a two-dimensional coordinate system. A gradient and intercept of a straight line, which passes the points or vicinity of the points, are obtained by least square approximation, and the suspected defective pattern is determined from the straight line according to the gradient and the intercept thereof, the wrinkle being determined by evaluating the suspected defective pattern.

The wrinkle is graded in prescribed grades according to a length of the straight line.

The surface defect is detected before winding the film in producing the film.

The length information is information for expressing the length of the dots stepwise in plural ranks.

The measuring step includes detecting image portions in the image data by edge point detection of image density. The image portions detected by the edge point detection are measured, so as to obtain the length information of the dots being photographed.

Each of the blocks in the length data table is constituted by a predetermined plural number of the dots.

An alarm signal is output when the surface defect is detected.

If a plurality of the surface defect are detected, a largest one of the plurality of the surface defect is selected.

The film is subjected to removal of the surface defect when the surface defect is detected.

Also, a surface defect inspector includes a transporting mechanism for transporting film on an inspecting surface having a color for absorbing light. A dot pattern test chart indicates a dot pattern having dots. An image pickup device photographs the dot pattern by image pickup upon reflection of the dot pattern on the film positioned on the inspecting surface. A determiner measures a length of the dots being photographed according to image data obtained by the image pickup, to obtain length information, creates a length data table of the dots by arranging the length information at locations of the dots, and determines occurrence of a surface defect at one of the locations if a difference between the dots occurs in the length information in the length data table.

Furthermore, a transparent test chart sheet is disposed to face the film, for constituting the test chart. A surface light source applies inspecting light to a rear of the test chart sheet, for passing through and becoming incident upon the film.

The test chart and the image pickup device are disposed higher than the inspecting roller. An angle defined between an optical axis of the surface light source and an optical axis of the image pickup device is equal to or more than 30 degrees and equal to or less than 60 degrees.

Also, a surface defect inspecting computer executable program includes a transporting program code for transporting film on an inspecting surface having a color for absorbing light. A photographing program code is for photographing a dot pattern having dots on a dot pattern test chart by image pickup upon reflection of the dot pattern on the film positioned on the inspecting surface. A measuring program code is for measuring a length of the dots being photographed according to image data obtained by the image pickup, to obtain length information. A creating program is code for creating a length data table of the dots by arranging the length information at locations of the dots. A determining program code is for determining occurrence of a surface defect at one of the locations if a difference between the dots occurs in the length information in the length data table.

Also, a surface defect inspecting user interface includes a transporting region for transporting film on an inspecting surface having a color for absorbing light. A photographing region is for photographing a dot pattern having dots on a dot pattern test chart by image pickup upon reflection of the dot pattern on the film positioned on the inspecting surface. A measuring region is for measuring a length of the dots being photographed according to image data obtained by the image pickup, to obtain length information. A creating region is for creating a length data table of the dots by arranging the length information at locations of the dots. A determining region is for determining occurrence of a surface defect at one of the locations if a difference between the dots occurs in the length information in the length data table.

BRIEF DESCRIPTION OF THE DRAWINGS

The above objects and advantages of the present invention will become more apparent from the following detailed description when read in connection with the accompanying drawings, in which:

FIG. 8A is a chart illustrating an image photographed by the video camera;

FIG. 8B is a table illustrating a length data table of photographed dots;

FIG. 8C is a table illustrating a set of blocks;

FIG. 8D is a chart illustrating suspected defective blocks and suspected defective pattern;

FIG. 12A is an explanatory view illustrating a test chart according to a known surface defect inspection;

FIG. 12B is an explanatory view illustrating an image of the test chart reflected by film to be inspected;

FIG. 12C is an explanatory view illustrating derived images of image portions from the image;

FIG. 13A is an explanatory view illustrating another preferred test chart with fine stripes; and FIG. 13B is an explanatory view illustrating an image of the test chart being reflected.

DETAILED DESCRIPTION OF THE PREFERRED EMBODIMENT(S) OF THE PRESENT INVENTION

Figure 1:
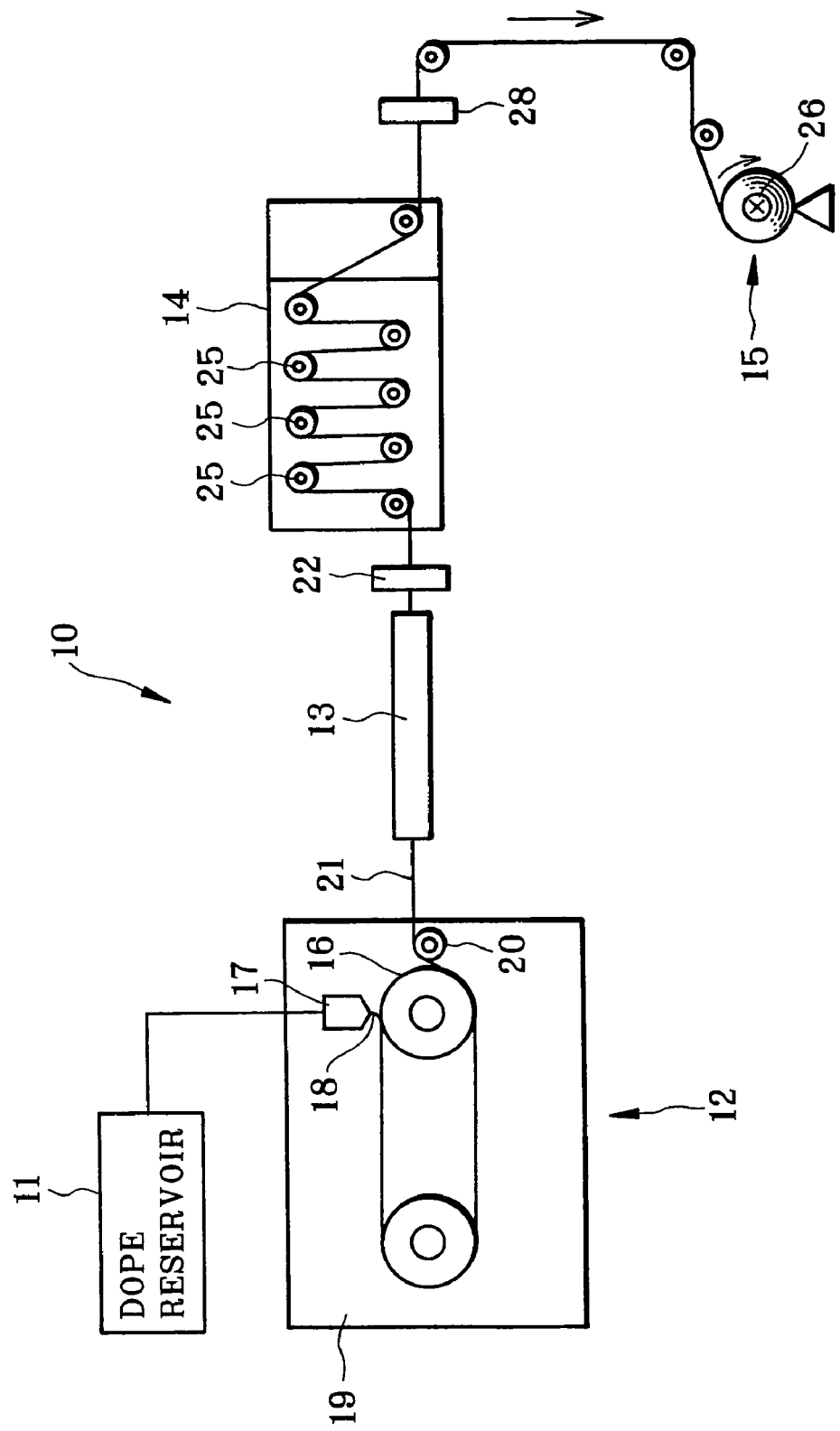
FIG. 1 is an explanatory view in elevation illustrating a polymer film producing system.

In FIG. 1, a surface defect inspector of the invention is used in producing cellulose acylate film. A polymer film producing system 10 includes a dope reservoir of production 11, a caster 12, a tentering machine 13, a drier 14, and a winder 15.

The dope reservoir 11 produces dope or polymer solution in dissolving or dispersing polymer in solvent. The caster 12 includes a casting band 16 and a casting die 17. The casting band 16 of stainless steel is caused to turn about. The casting die 17 casts dope 18 on to the casting band 16. A casting chamber 19 contains the casting band 16. Dry gas is caused to flow along the casting band 16, and quickens drying of a cast film of the dope 18 on the casting band 16, by evaporating solvent. When the cast film comes to have a self-supporting property, a stripping roller 20 strips the cast film, which is polymer film 21 obtained as self-supporting cast film 21.

The polymer film 21 obtained from the casting band 16 has the self-supporting property, but still contains much solvent. The polymer film 21 is dried sufficiently by the tentering machine 13 and the drier 14. In the tentering machine 13, selvedges of the polymer film 21 are grasped by clip mechanisms, while the polymer film 21 is transported and dried at the same time. An edge slitter 22 receives the polymer film 21 exited from the tentering machine 13, and cuts away the selvedge portions of the polymer film 21.

Plural drying rollers 25 are contained in the drier 14. When the polymer film 21 is exited from the edge slitter 22, the polymer film 21 is transported in contact with the drying rollers 25, and becomes dried by evaporating the solvent sufficiently. After this, a spindle 26 in the winder 15 winds the polymer film 21.

Figure 2:
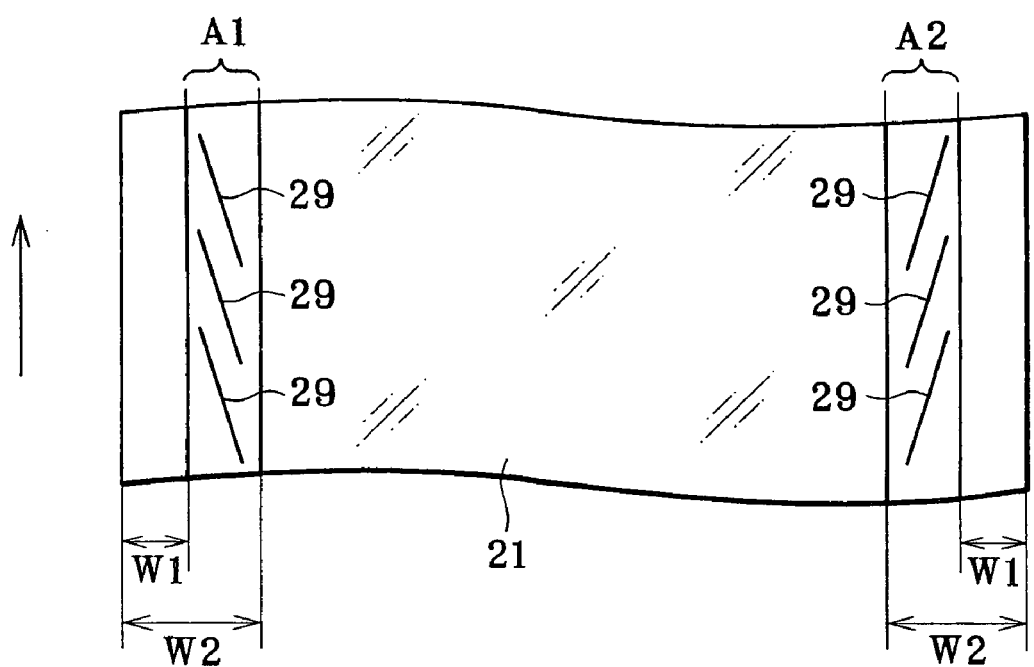
FIG. 2 is a plan, partially broken, illustrating film together with inclined wrinkles.

A surface defect inspector 28 for wrinkles according to the invention is disposed upstream from the winder 15. Fine wrinkles with an inclination are detected by the surface defect inspector 28 as surface defects. In FIG. 2, inclined wrinkles 29 or surface defects as a target of detection are likely to occur in regions A1 and A2, each of which is defined between a line at a distant W1 from an edge of the polymer film 21 and a line at a distant W2 from the edge of the polymer film 21. The distances W1 and W2 may vary. According to the embodiment, W1 is approximately 50 mm. W2 is approximately 150 mm. A height of the wrinkles 29 in the direction vertical to the film surface is generally estimated equal to or less than 10 microns. A width of the wrinkles 29 is approximately 2 mm. A length of the wrinkles 29 is 250-300 mm.

Figure 3:
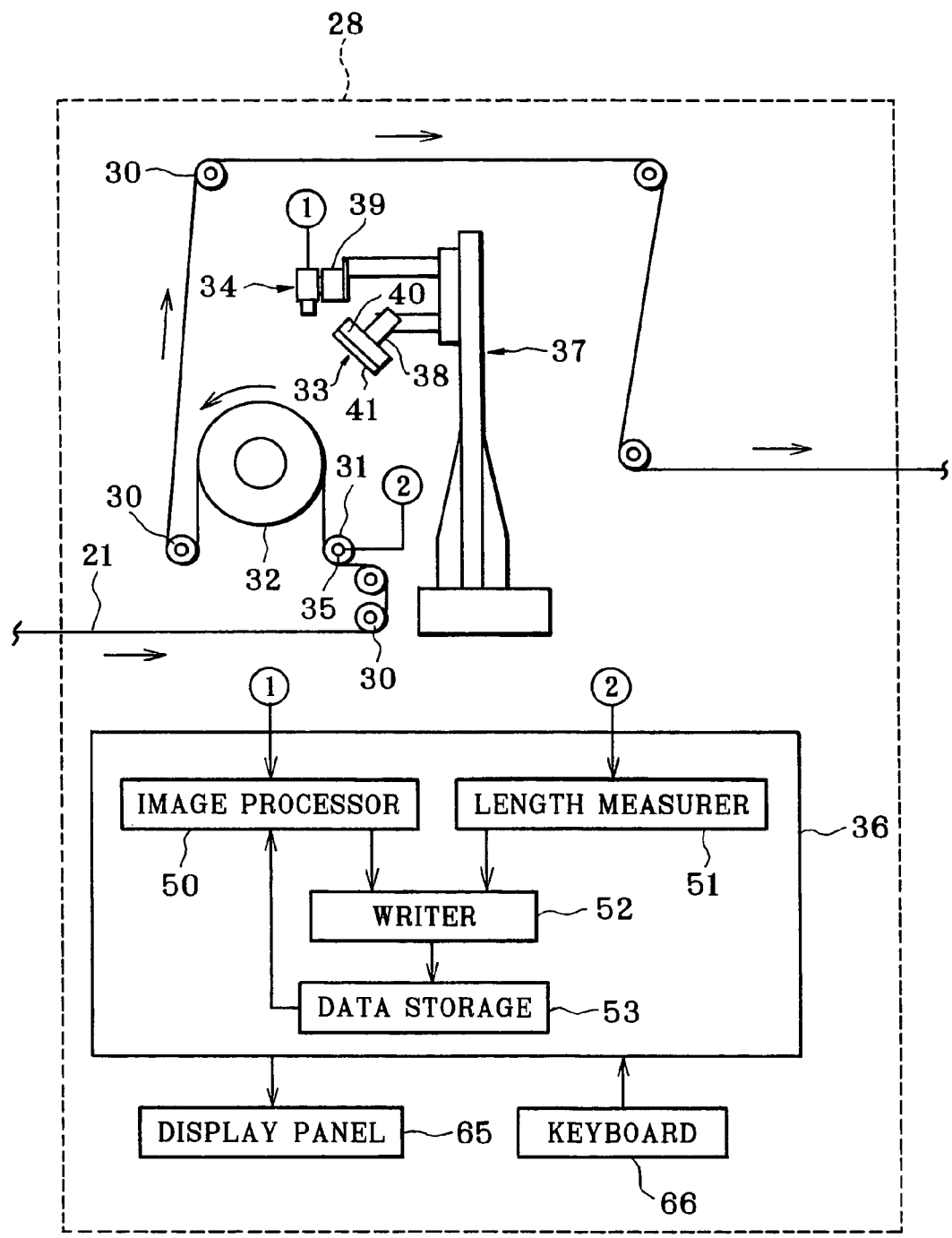
FIG. 3 is an explanatory view in elevation illustrating a surface defect inspector for wrinkles.

In FIG. 3, the surface defect inspector 28 includes a free roller 31 together with a transporting mechanism, a backup roller 32 as an inspecting roller with an inspecting surface, a dot pattern indicator 33 with a test chart, a video camera 34 having an image pickup device, a pulse generator 35, and a system controller 36 as a determiner. The pulse generator 35 is associated axially with the free roller 31. The pulse generator 35 generates pulses of the number according to the movement of the polymer film 21. A length measurer 51 in the system controller 36 is provided with the pulses. Transport rollers 30 as transport mechanism transport the polymer film 21 at a speed, for example at 60 meters per second.

Figure 6:
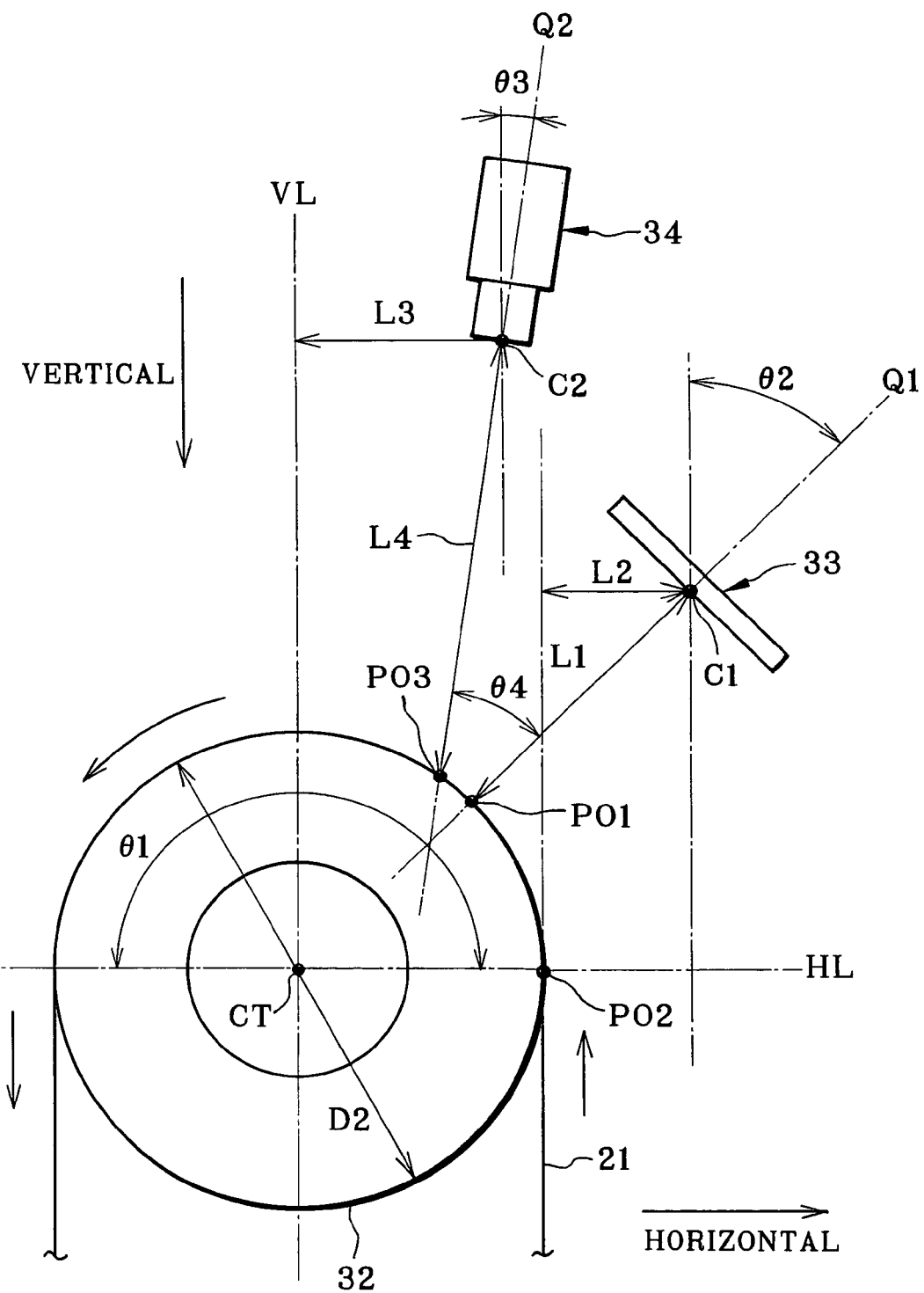
FIG. 6 is an explanatory view in elevation illustrating the same as FIG. 5.

The backup roller 32 supports the polymer film 21 and guides the polymer film 21 being transported, and has a black surface finished by mat finish without gloss. The surface of the polymer film 21 can reflect incident light. As will be described later, light with a dot pattern on the dot pattern indicator 33 is reflected by the polymer film 21 and photographed by the video camera 34. A diameter D1 of the backup roller 32 of FIG. 6 is equal to or more than 250 mm and equal to or less than 700 mm, and preferably equal to or more than 250 mm and equal to or less than 500 mm. Note that an upper limit of the diameter D1 may be still greater despite those values, if an area to be photographed for the dot pattern on the surface of the polymer film 21 can be kept sufficiently large. A wrap angle θ1 of the polymer film 21 of FIG. 6 is equal to or more than 120 degrees and equal to or less than 180 degrees.

A support 37 is installed to support the dot pattern indicator 33 and the video camera 34 in the vicinity of the backup roller 32. Bracket shaped fine adjusters 38 and 39 keep the dot pattern indicator 33 and the video camera 34 secured to the support 37 in a finely adjustable manner for the position.

The dot pattern indicator 33 includes a surface light source 40 and a transparent test chart sheet 41 attached to a surface of the surface light source 40. The surface light source 40 has a structure including a great number of light emitting diodes (LEDs) arranged two-dimensionally. Alternatively, the surface light source 40 can be constructed by a halogen lamp, a fluorescent lamp, or other illuminating device. A photo sensor (not shown) may be incorporated in the surface light source 40 if required, for feedback control of a light amount by use of a photo sensor output. A diffusion plate (not shown) is disposed between the surface light source 40 and the test chart sheet 41 for removing irregularity in the light emission.

Figure 4:
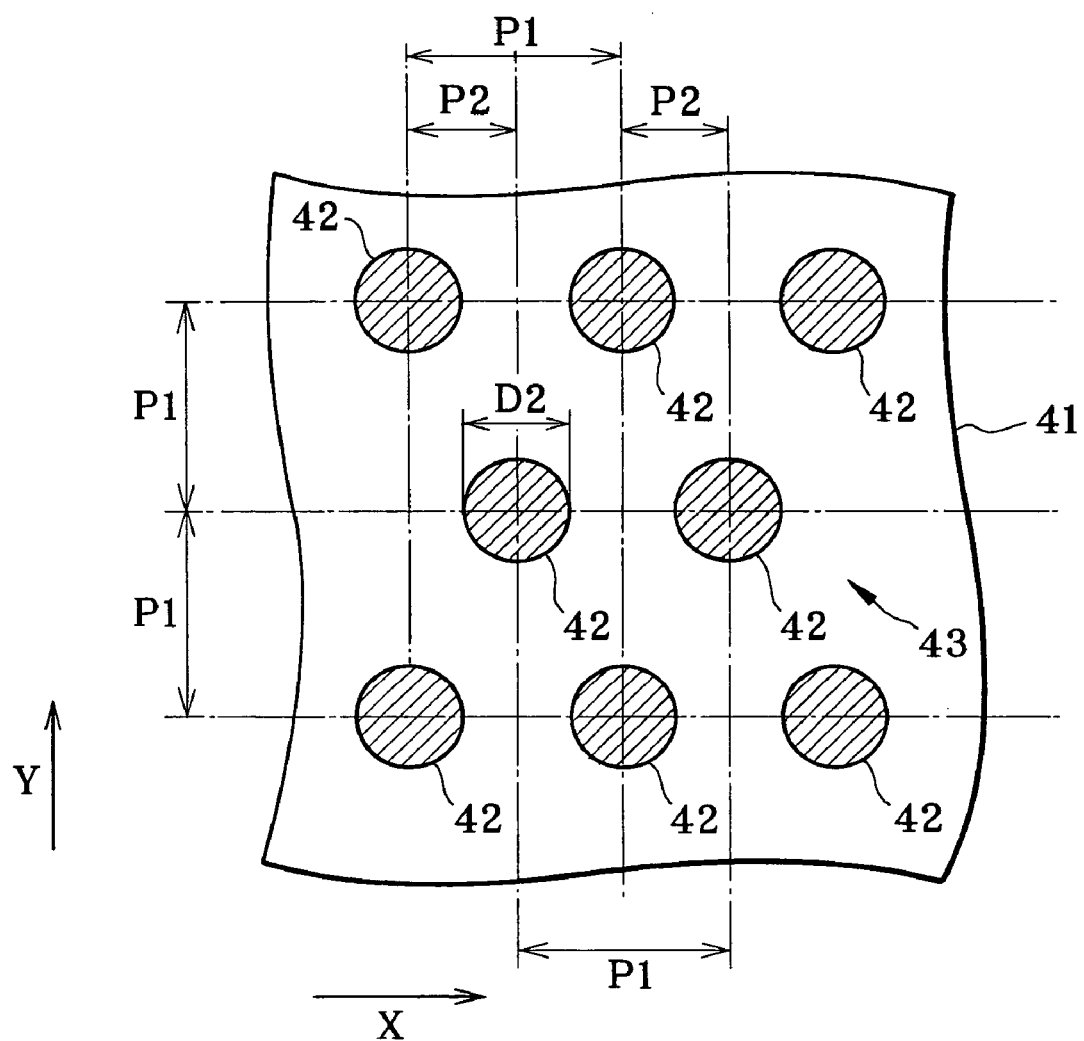
FIG. 4 is a plan, partially broken, illustrating a dot pattern in a test chart sheet.

In FIG. 4, a dot pattern 43 or a test chart is printed on the test chart sheet 41. A great number of dots 42 in the dot pattern 43 are arranged in a two-dimensional manner. The dots 42 have shapes of circles with a diameter D2. The diameter D2 is determined suitably according to a height or other size of the wrinkles 29 to be detected. The diameter D2 is in a range equal to or more than 1 mm and equal to or less than 3 mm, and preferably can be in a range equal to or more than 1.5 mm and equal to or less than 2.5 mm. The dots 42 are arranged at a pitch P1 in the direction X of transport of the polymer film 21. The pitch P1 is in a range equal to or more than 3 mm and equal to or less than 5 mm, and preferably can be in a range equal to or more than 3.5 mm and equal to or less than 4.5 mm. Arrays of the dots 42 extending in the direction X are arranged at a pitch P1 in the direction Y. In relation to a first array and a second array next to the first in the direction Y, the dots 42 are positioned in a zigzag, namely are offset in the direction X at a pitch P2 between the first and second arrays. The pitch P2 is in a range equal to or more than 1 mm and equal to or less than 4 mm, and preferably can be in a range equal to or more than 1 mm and equal to or less than 3 mm. Note that the dots 42 are circular, but may be in any looped shape, such as a quadrilateral, ellipse, polygon and other forms. Also, the color of the dots 42 may be such having high density other than the black color, so that portions with and without the dots 42 can be discerned clearly in the subsequent step of the image processing.

The video camera 34 picks up a reflected image of the dot pattern 43 of the dot pattern indicator 33 from the polymer film 21 supported on the backup roller 32 or inspecting roller in a region of 100×1,000 mm. An example of the video camera 34 is a High Speed Random Camera manufactured by Matsushita Electric Works, Ltd. Motion picture data of the video camera 34 is intermittently retrieved as image data of still images. An image processor 50 in the system controller 36 as a determiner is provided with the image data.

Figure 5:
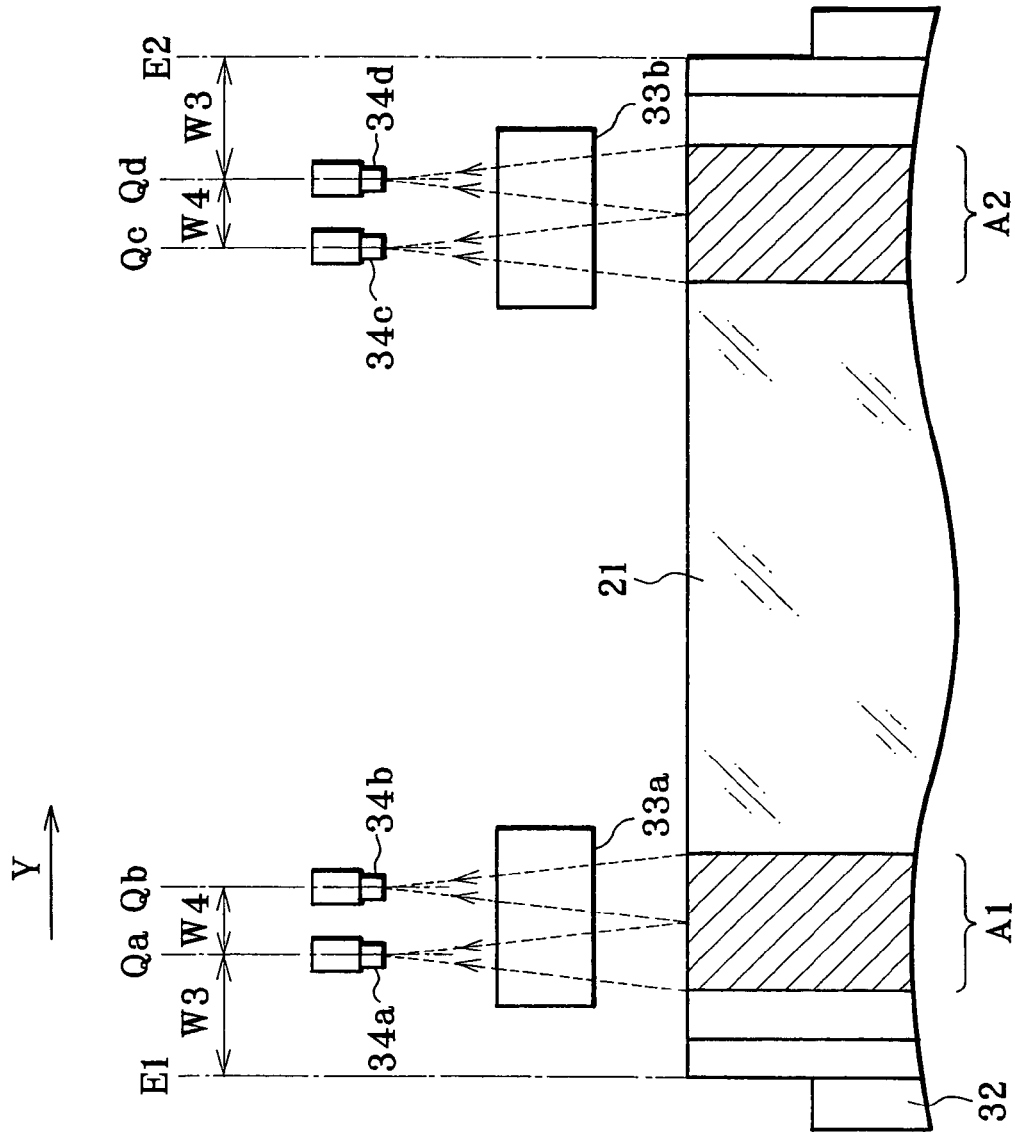
FIG. 5 is a front elevation, partially broken, illustrating a relationship between a backup roller and four image pickup devices.

In FIG. 5, two dot pattern indicators 33a and 33b are disposed for regions A1 and A2 where wrinkles are created. Each of the regions A1 and A2 is considerably large. Thus, two image pickup devices or cameras 34a and 34b are disposed for the region A1 on a first side of the polymer film 21.

Two image pickup devices or cameras 34c and 34d are disposed for the region A2 on a second side of the polymer film 21. Let W3 be a distance between an optical axis Qa of the image pickup device 34a and an end line E1 of the backup roller 32. W3 is 230 mm. A distance between an optical axis Qd of the image pickup device 34d and an end line E2 of the backup roller 32 is also W3. According to this, the image pickup devices 34a and 34d are positioned. Let W4 be a distance between an optical axis Qb of the image pickup device 34b and the optical axis Qa. W4 is 55 mm. A distance between an optical axis Qc of the image pickup device 34c and the optical axis Qd is also W4. According to this, the image pickup devices 34b and 34c are positioned. Note that the number of the image pickup devices 34a-34d can be varied according to the sizes of the regions A1 and A2. In view of the plurality, image data of photographing regions of the image pickup devices 34a-34d are evaluated for processing of pattern matching. Borderlines between the photographing regions are determined for the purpose of combining partial images.

In FIG. 6, an example of arrangement of the dot pattern indicator 33 and the video camera 34 is illustrated with reference to the backup roller 32 or inspecting roller. An optical axis Q1 of the dot pattern indicator 33 is inclined with reference to the vertical line at an angle θ2 of 45 degrees. A distance L1 from the center C1 of the dot pattern indicator 33 to the peripheral surface PO1 of the backup roller 32 is 150 mm. A distance L2 from the center C1 of the dot pattern indicator 33 to the peripheral surface PO2 of the backup roller 32 in the horizontal direction is 50 mm. Thus, the dot pattern indicator 33 is positioned. For the video camera 34, a distance L3 from the center C2 of the taking lens of the video camera 34 to the center CT of the backup roller 32 in the horizontal direction is 75 mm. An optical axis Q2 of the video camera 34 is inclined with reference to the vertical line at an angle θ3 of 5 degrees. A distance L4, from the center C2 of the taking lens to an intersection point PO3 between the optical axis Q2 and the peripheral surface of the backup roller 32, is 235 mm. Note that a view angle θ4 of the video camera 34, which is defined between the optical axes Q1 and Q2, is equal to or more than 30 degrees and equal to or less than 60 degrees. A display region of the dot pattern indicator 33 is 240×270 mm.

The system controller 36 includes a writer 52, a data storage 53, the image processor 50 and the length measurer 51. A display panel 65 and a keyboard 66 as a user interface are connected with the system controller 36. The length measurer 51 receives pulses from the pulse generator 35, and measures length data with reference to a front end of the polymer film 21. The length data is transmitted to the writer 52, where defect data is produced by combining the length data with the wrinkle data transmitted by the image processor 50. The defect data is evaluated to determine a position of the wrinkle. The defect data is written to the data storage 53. Also the data storage 53 stores required information for checking wrinkles, such as size information of a dot length as reference of quantifying the dot length. The information is changeable by use of the keyboard 66 if required.

The image processor 50 retrieves image data from the video camera 34 in a regular sequential manner in synchronism with pulses generated by the pulse generator 35. Image data is processed according to image processing, so it is checked according to the processing whether a wrinkle has occurred or not. If the known image processing of FIGS. 12 and 13 is used, time for the image processing of image data of one image is approximately 4.5 seconds. In contrast, time for the image processing of one image is approximately 1/150 second according to the invention. The time required for image processing can be shortened considerably according to the invention. Note that use of higher performance of CPU may also shorten the required time.

Figure 7:
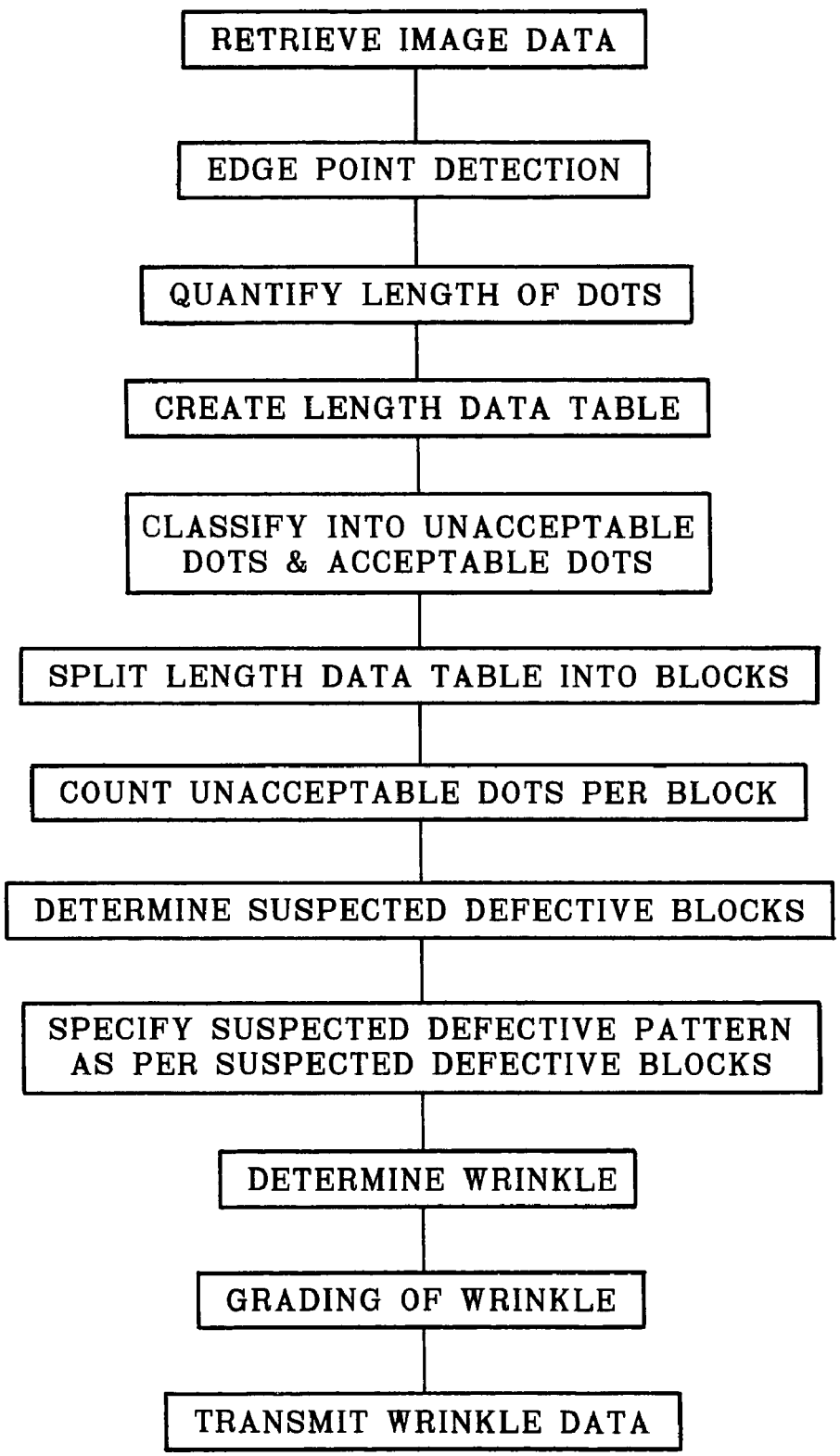
FIG. 7 is a flow chart illustrating image processing.

Processing operation in the image processor 50 is hereafter described. In FIG. 7, a flow of the processing is illustrated. In FIG. 8A, image data 55 from the video camera 34 is illustrated. Dots 56 of elliptically deformed shapes are picked up as a result of a deformed shape of the backup roller 32 or inspecting roller. The image processor 50 processes the image data for edge point detection of image density. Among portions of an image of the image data 55, one portion having an abrupt change in the density is discriminated as an edge, to detect the position of the edge. Thus, the dots 56 are discerned by the density according to the edge point detection of image density, to determine the edge position with reference to the direction X of the polymer film 21. The existence between edges of the dots is measured by counting the converted number of pixels, to determine the length information of the dots 56. The number is quantified in a stepwise form of five ranks according to the converting standard information predetermined and stored, to output length information of 1-5. The length information 1 expresses the shortest dot. The length information 5 expresses the longest dot. In the present embodiment, the number of the ranks of the dot length is five. However, the number of the ranks may be changed according to the size of a wrinkle.

In FIG. 8B, a length data table 58 is depicted, in which quantified values of dot lengths are arranged according to locations of the dots 56 on the image data 55.

The dots 56 are next classified into unacceptable dot information 56a and acceptable dot information 56b in the length data table 58 according to the quantified dot lengths. The unacceptable dot information 56a is defined according to such included in the dots 56 and having the dot length of 1 or 5 due to changes caused by possible wrinkles. The acceptable dot information 56b is defined according to such included in the dots 56 and having the dot length of 2, 3 or 4 owing to a state without large changes. Note that the numerals of the unacceptable and acceptable dot information 56a and 56b are indicated at limited portions of the dots 56 for the simplification. It is alternatively possible to define the unacceptable dot information 56a according to such included in the dots 56 and having the dot length of 1, 2, 4 or 5, and to define the acceptable dot information 56b according to the dot length of only 3.

In FIG. 8C, blocks 59 are defined by regularly splitting the length data table 58. Dots of the unacceptable dot information 56a are counted in the blocks 59. In the embodiment, each of the blocks 59 is determined by dots of 2×2. However, each one block may be constituted by dots arranged in a selected form from 3×3, 4×4, 5×5, 5×3, 3×5 and the like. In FIG. 8D, there is one or more dots with the unacceptable dot information 56a within the blocks 59. Then it is judged that the block 59 is one of suspected wrinkle blocks 59a as suspected defective blocks. In the embodiment, the reference for determining the suspected wrinkle blocks 59a is one or more dots with the unacceptable dot information 56a. However, the number of dots as a reference with the unacceptable dot information 56a may be changed suitably.

A suspected wrinkle pattern 60 as suspected defective pattern is specified as a set of consecutive suspected wrinkle blocks 59a in any one of vertical, horizontal or diagonal directions. Then the number of the suspected wrinkle blocks 59a in the suspected wrinkle pattern 60 is evaluated so as to check whether the suspected wrinkle pattern 60 is a wrinkle. If it is, then the suspected wrinkle pattern 60 is evaluated for a grade of wrinkles. In the present embodiment, the suspected wrinkle pattern 60 is determined as a wrinkle if the number of the suspected wrinkle blocks 59a in the suspected wrinkle pattern 60 is two or more. Also, the wrinkles are graded in plural grades, namely grade A for the six suspected wrinkle blocks 59a, grade B for the five suspected wrinkle blocks 59a, grade C for the four suspected wrinkle blocks 59a, grade D for the three suspected wrinkle blocks 59a, and grade E for the two suspected wrinkle blocks 59a. A specific example is illustrated in FIG. 8D. The suspected wrinkle pattern 60 contains vertically consecutive three suspected wrinkle blocks 59a. The suspected wrinkle pattern 60 is determined as a wrinkle, and graded with grade D. Note that the number of the grades of the wrinkles can be changed if desired. Also, the number of the suspected wrinkle blocks 59a as reference number for grading may be changed in a manner different from the present embodiment.

Figure 9:
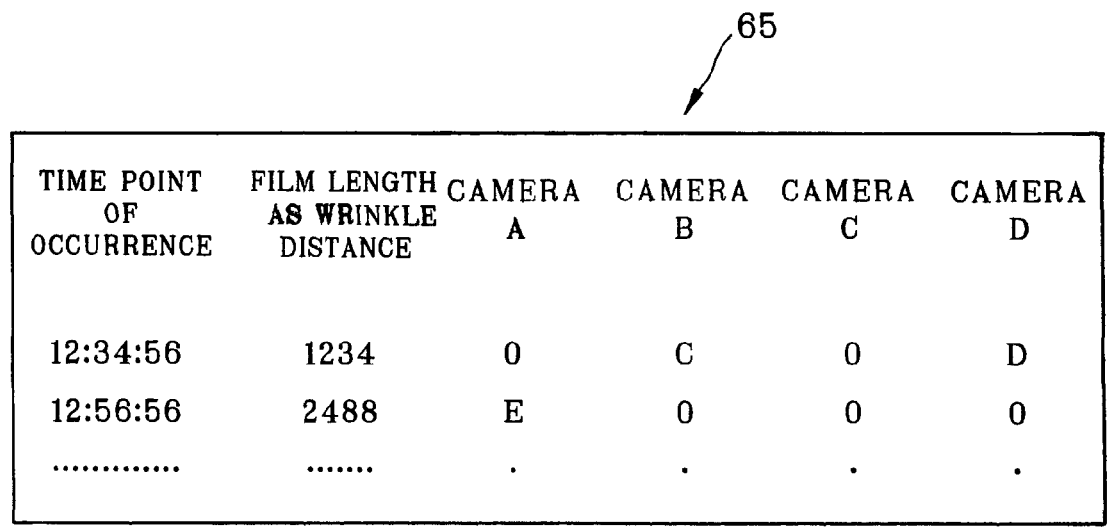
FIG. 9 is a table illustrating an example of defect data displayed on a user interface.

A result of processing of the image processor 50 is wrinkle data which is transmitted to the writer 52 of FIG. 3. The writer 52 creates defect data by combining the wrinkle data and the measured length data described above and writes the defect data to the data storage 53. Also, time point data is additionally included in the defect data, and is information of the time point of occurrence of a wrinkle. In FIG. 9, information is displayed on the display panel 65 according to defect data stored in the data storage 53, the information including the time point of occurrence of the wrinkle, a distance from a front end of the polymer film 21 to a position of the wrinkle, a grade of the wrinkle detected through the image pickup devices 34a-34d. Also, an alarm device (not shown) is driven to generate an alarm signal. The alarm device is driven if all the grades detected through the image pickup devices 34a-34d are E or higher. Alternatively, it is possible for example to drive the alarm device if at least one of the grades is A or higher according to the image pickup devices 34a-34d.

Note that if the alarm device is driven, production of the polymer film 21 may be interrupted for maintenance. Also, defect data stored in the data storage 53 may be written successively to an external storage device such as a hard disk drive (not shown). Also, the defect data may be converted into and kept in data files of .csv format for the purpose of editing in a spreadsheet program or the like.

In the present embodiment, the dot pattern 43 is indicated by the dot pattern indicator 33 including the test chart sheet 41 having the dot pattern 43 and the surface light source 40. However, the dot pattern 43 may be displayed in any other suitable manners. For example, an liquid crystal display device (LCD), cathode ray tube (CRT) and the like may be driven to display the dot pattern 43.

In the embodiment, image data is retrieved intermittently from motion picture data of the video camera 34 for the purpose of image processing. It is also possible to use a technique of pattern recognition to detect deformed state of dots in the course of running of the polymer film 21. There occurs distortion of each one of dots in the dot pattern at each time that a portion of the wrinkle passes. It is possible to obtain an average of the distortion amounts of the dots, and to create the length data table 58 according to the average of the distortion amounts.

Figure 10:
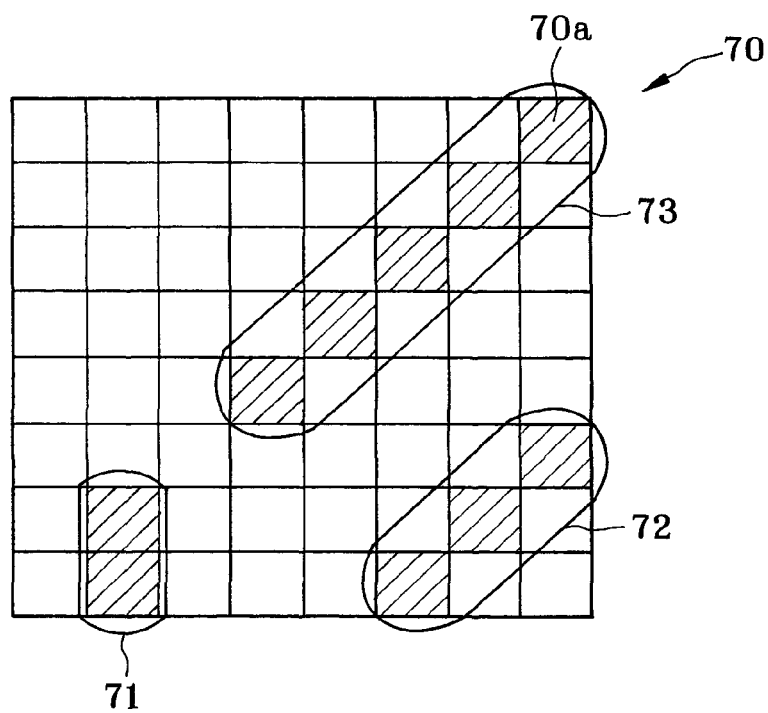
FIG. 10 is a chart illustrating plural suspected defective patterns.

In the above embodiment, only one suspected defective pattern is found in image data. Furthermore, image processing at the time that two or more suspected defective patterns are found in image data is described now. Blocks 70 having predetermined areas are depicted in FIG. 10. Suspected wrinkle blocks 70a as suspected defective blocks are hatched in the drawing. Note that in FIG. 10, the numeral of 70a is indicated at a limited portion for the simplification. A suspected wrinkle pattern 71 as suspected defective pattern is constituted by two vertically consecutive suspected wrinkle blocks 70a. A suspected wrinkle pattern 72 as suspected defective pattern is constituted by three diagonally consecutive suspected wrinkle blocks 70a. A suspected wrinkle pattern 73 as suspected defective pattern is constituted by five diagonally consecutive suspected wrinkle blocks 70a. The suspected wrinkle pattern 73 is regarded as the most important because of the highest number of the suspected wrinkle blocks 70a, and determined as a wrinkle. According to the grading described above, the suspected wrinkle pattern 73 is evaluated as grade B. Note that all of plural suspected wrinkle patterns may be evaluated and then graded.

In the embodiment, a suspected wrinkle pattern having the suspected wrinkle blocks 70a of at least a predetermined number and consecutive in any direction is regarded as the wrinkle 29. However, it is possible to define points in a two-dimensional coordinate system by the suspected wrinkle blocks 70a. A suspected wrinkle pattern can be determined according to the points to detect the wrinkle 29. This is advantageous even when the method of the above embodiment is not very effective, for example when a couple of adjacent blocks among the suspected wrinkle blocks 70a do not exist. Specifically, the least square approximation is applied by use of the points associated with the suspected wrinkle blocks 70a. A straight line which passes the points or passes the vicinity of the points is regarded as a suspected wrinkle pattern. Then the wrinkle 29 is detected according to the straight line.

Figure 11A:
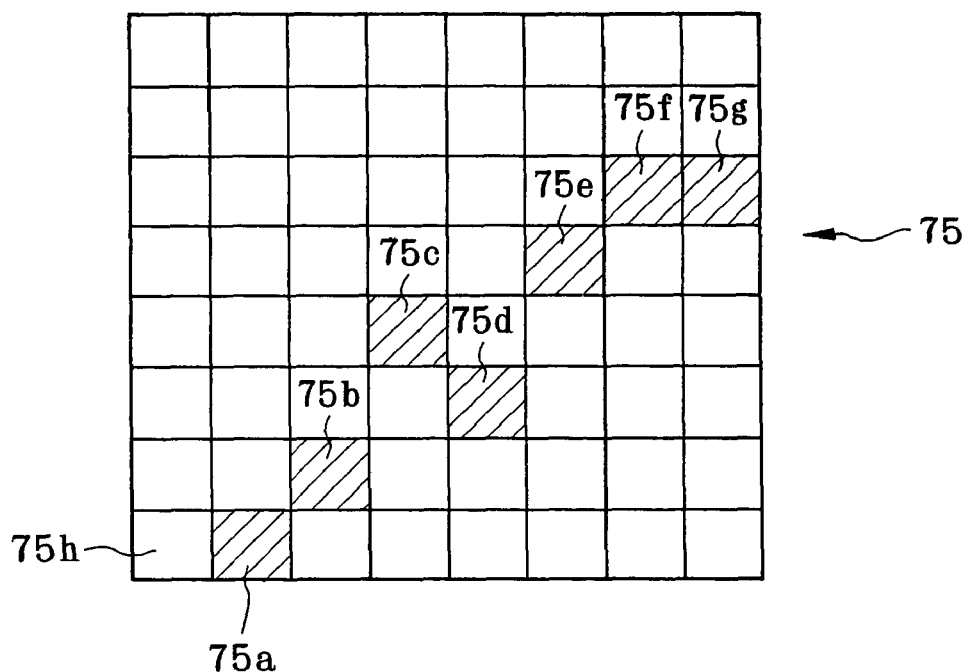
FIG. 11A is a chart illustrating suspected defective blocks in an embodiment where least spare approximation is used.
Figure 11B:
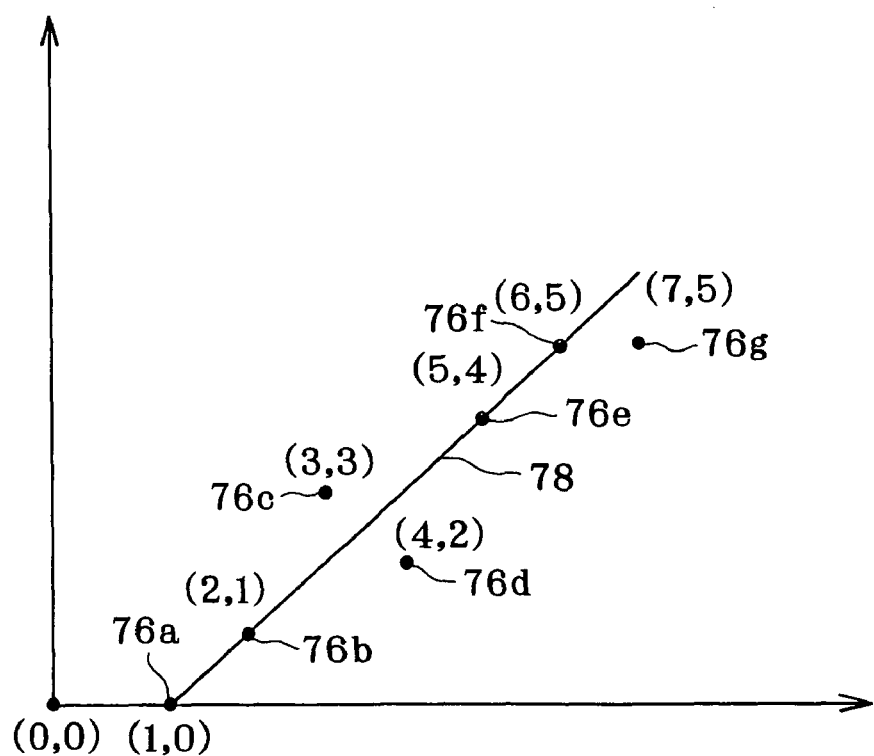
FIG. 11B is a graph illustrating points related to the suspected defective blocks.

In FIG. 11A, blocks 75 have a respectively predetermined area. Suspected wrinkle blocks 75a-75g as suspected defective blocks are hatched in the drawing. In FIG. 11B, a block 75h of FIG. 11A is determined as an original point. Points 76a-76g are defined on the coordinate system of the two dimensions, and associated with the suspected wrinkle blocks 75a-75g. A straight line 78 is derived from the points 76a-76g to pass those or to pass the vicinity of those according to least square approximation known in the art. A gradient and intercept of the straight line 78 are calculated. In the specific case, the gradient of the straight line 78 is 1. Its intercept is −1. The gradient and intercept are evaluated. If those are found in a predetermined wrinkle range, then the straight line 78 with those is determined as a wrinkle. After this, a plurality of wrinkles are classified according to the length of the straight line 78 or a distance between the end points of the straight line 78. In the specific case, the length of the straight line 78 is $6 \times 2^{1/2}$. This is subjected to the classification.

In the above embodiments, information of sound is generated for alarm of defect according to defect data. In place of this or in addition to this, suppression of occurrence of the wrinkles 29 can be automated in a manner of on-line in the polymer film producing system 10. For example, a suction duct for removing dust is associated with the tentering machine 13 on lateral portions of the polymer film 21 in the vicinity of stripping of the polymer film 21. An amount or direction of suction for gas is controlled through the suction duct. Wrinkles can be prevented by absorbing on the lateral portion of the polymer film 21. Also, looseness of the polymer film 21 can be absorbed by changing a wrap angle of a sealing roller between the tentering machine 13 and the drier 14. Furthermore, the looseness of the polymer film 21 can be absorbed also by adding a small roll for supporting selvedge portions of the polymer film 21, and by changing tension applied to the selvedge portions after the slitting.

Also, known techniques in the field of defect inspection and strain inspection may be added in the invention in combination with the above embodiments.

Although the present invention has been fully described by way of the preferred embodiments thereof with reference to the accompanying drawings, various changes and modifications will be apparent to those having skill in this field. Therefore, unless otherwise these changes and modifications depart from the scope of the present invention, they should be construed as included therein.

What is claimed is:

1. A surface defect inspecting method comprising steps of:
transporting film on an inspecting surface having a color for absorbing light;
photographing a dot pattern having dots on a dot pattern test chart by image pickup upon reflection of said dot pattern on said film positioned on said inspecting surface;
measuring a length of said dots being photographed according to image data obtained by said image pickup, to obtain length information;
creating a length data table of said dots by arranging said length information at locations of said dots; and
determining occurrence of a surface defect at one of said locations if a difference between said dots occurs in said length information in said length data table.

2. A surface defect inspecting method as defined in claim 1, wherein said dots have a diameter equal to or more than 1 mm and equal to or less than 3 mm, and are arranged at a pitch equal to or more than 3 mm and equal to or less than 5 mm.

3. A surface defect inspecting method as defined in claim 1, wherein said dots are arranged so that dots in a first dot array thereof are offset in a zigzag manner from dots in a second dot array thereof.

4. A surface defect inspecting method as defined in claim 3, wherein said dots have a black color.

5. A surface defect inspecting method as defined in claim 3, wherein a transparent test chart sheet constitutes said test chart and is disposed to face said film;
inspecting light is applied to a rear of said test chart sheet, passes through, and becomes incident upon said film.

6. A surface defect inspecting method as defined in claim 5, wherein said inspecting surface is a peripheral surface of an inspecting roller, and a diameter of said inspecting roller is equal to or more than 250 mm and equal to or less than 500 mm.

7. A surface defect inspecting method as defined in claim 6, wherein said peripheral surface of said inspecting roller is finished by mat finish.

8. A surface defect inspecting method as defined in claim 6, wherein said film contacts on said inspecting roller at a wrap angle equal to or more than 120 degrees and equal to or less than 180 degrees.

9. A surface defect inspecting method as defined in claim 8, wherein said determining step includes:
classifying said dots into an acceptable dot and an unacceptable dot in said length data table according to said length;
splitting said length data table into blocks with a prescribed area, to acquire amounts of said unacceptable dot per said blocks;
if said amounts of said unacceptable dot per said blocks are more than a prescribed value, determining suspected defective blocks therewith retrieved among said blocks;
defining a suspected defective pattern by continuation of adjacent suspected defective blocks among said suspected defective blocks;
said surface defect is determined from said suspected defective pattern by evaluating a shape thereof.

10. A surface defect inspecting method as defined in claim 9, wherein said acceptable dot has a length of length information equal to a predetermined middle rank length information, and said unacceptable dot has a length of length information higher or lower than said predetermined middle rank length information.

11. A surface defect inspecting method as defined in claim 9, wherein said surface defect is constituted by a wrinkle on said film.

12. A surface defect inspecting method as defined in claim 11, wherein adjacent suspected defective blocks being consecutive in any one of vertical, horizontal and diagonal directions are retrieved among said suspected defective blocks, and combined to define a defective pattern, and said wrinkle is constituted by said defective pattern.

13. A surface defect inspecting method as defined in claim 12, wherein said wrinkle is graded in prescribed grades according to a number of said suspected defective blocks.

14. A surface defect inspecting method as defined in claim 11, wherein said suspected defective blocks are plotted at points defined on a two-dimensional coordinate system;
a gradient and intercept of a straight line, which passes said points or vicinity of said points, are obtained by least square approximation, and said suspected defective pattern is determined from said straight line according to said gradient and said intercept thereof, said wrinkle being determined by evaluating said suspected defective pattern.

15. A surface defect inspecting method as defined in claim 14, wherein said wrinkle is graded in prescribed grades according to a length of said straight line.

16. A surface defect inspecting method as defined in claim 15, wherein said surface defect is detected before winding said film in producing said film.

17. A surface defect inspecting method as defined in claim 1, wherein said length information is information for expressing said length of said dots stepwise in plural ranks.

18. A surface defect inspecting method as defined in claim 1, wherein said measuring step includes:
detecting image portions in said image data by edge point detection of image density; and
measuring said image portions detected by said edge point detection, so as to obtain said length information of said dots being photographed.

19. A surface defect inspecting method as defined in claim 1, wherein each of said blocks in said length data table is constituted by a predetermined plural number of said dots.

20. A surface defect inspecting method as defined in claim 1, wherein an alarm signal is output when said surface defect is detected.

21. A surface defect inspecting method as defined in claim 1, wherein if a plurality of said surface defect are detected, a largest one of said plurality of said surface defect is selected.

22. A surface defect inspecting method as defined in claim 1, wherein said film is subjected to removal of said surface defect when said surface defect is detected.

23. A surface defect inspector comprising:
a transporting mechanism for transporting film on an inspecting surface having a color for absorbing light;
a dot pattern test chart for indicating a dot pattern having dots;
an image pickup device for photographing said dot pattern by image pickup upon reflection of said dot pattern on said film positioned on said inspecting surface;
a determiner for measuring a length of said dots being photographed according to image data obtained by said image pickup, to obtain length information, for creating a length data table of said dots by arranging said length information at locations of said dots, and for determining occurrence of a surface defect at one of said locations if a difference between said dots occurs in said length information in said length data table.

24. A surface defect inspector as defined in claim 23, further comprising:
a transparent test chart sheet, disposed to face said film, for constituting said test chart;
a surface light source for applying inspecting light to a rear of said test chart sheet, for passing through and becoming incident upon said film.

25. A surface defect inspector as defined in claim 23, wherein said inspecting surface is a peripheral surface of an inspecting roller, and a diameter of said inspecting roller is equal to or more than 250 mm and equal to or less than 500 mm.

26. A surface defect inspector as defined in claim 25, wherein said peripheral surface of said inspecting roller is finished by mat finish.

27. A surface defect inspector as defined in claim 25, wherein said film contacts on said inspecting roller at a wrap angle equal to or more than 120 degrees and equal to or less than 180 degrees.

28. A surface defect inspector as defined in claim 25, wherein said test chart and said image pickup device are disposed higher than said inspecting roller;
an angle defined between an optical axis of said surface light source and an optical axis of said image pickup device is equal to or more than 30 degrees and equal to or less than 60 degrees.

* * * * *